United States Patent [19]

Rossiter

[11] 4,405,235

[45] Sep. 20, 1983

[54] LIQUID CELL FOR SPECTROSCOPIC ANALYSIS

[76] Inventor: Val J. Rossiter, 16 Rathmore Ave., Stillorean, Dublin, Ireland

[21] Appl. No.: 245,427

[22] Filed: Mar. 19, 1981

[51] Int. Cl.³ .............................................. G01N 21/05
[52] U.S. Cl. ..................................... 356/246; 356/440
[58] Field of Search ......................... 356/246, 440, 410

[56] References Cited

U.S. PATENT DOCUMENTS

| | | | |
|---|---|---|---|
| 2,649,011 | 8/1953 | Black | 356/246 |
| 2,954,472 | 9/1960 | Frenzel | 356/246 X |
| 3,773,424 | 11/1973 | Selgin | 356/246 X |
| 3,999,867 | 12/1976 | Stabell | 356/246 |

Primary Examiner—Vincent P. McGraw
Attorney, Agent, or Firm—Sughrue, Mion, Zinn, Macpeak and Seas

[57] ABSTRACT

A liquid cell for use in spectroscopic analysis of flowing liquids formed by a front plate (1) as an optical window, a back plate (2) providing a reflecting surface (6), and a sealing means (3) between the two plates. In the back plate there are entry part (4) and exit part (5) for liquids to the cell. This arrangement is convenient to connect for liquid through-put, and gives extra sensitivity and allows detection of very small quantities of material present in the flow.

10 Claims, 2 Drawing Figures

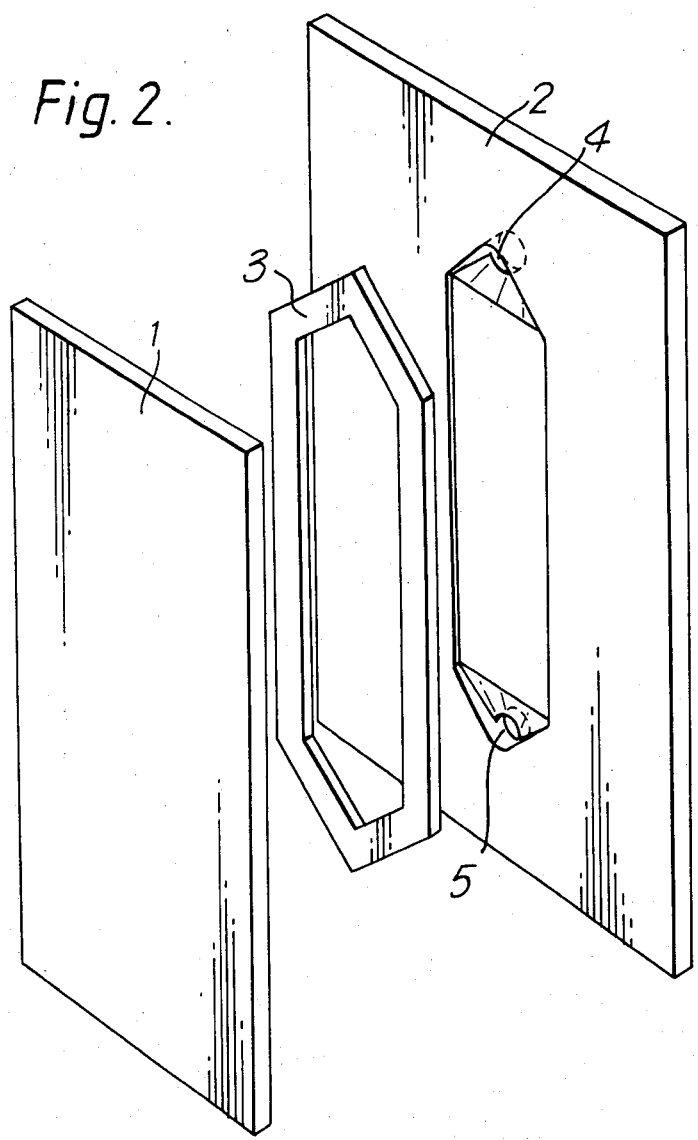

LIQUID CELL FOR SPECTROSCOPIC ANALYSIS

This invention relates to a liquid cell for use in spectroscopic analysis of flowing liquids.

In conventional liquid cells for this purpose light is shone through a cell formed by two parallel windows with the liquid flowing therebetween. Problems arise with introducing liquid into such cells.

According to the invention there is provided a liquid cell defined by a front plate forming an optical window, a back plate providing a reflecting surface, sealing means for retaining liquid between the plate and entry and exit parts for liquid to the cell.

By having a reflecting back plate it is far easier to provide for connections for leading the liquid to the cell which do not interfere with the optical system. In a preferred embodiment the entry and exit ports are formed in the back plate, with the reflecting surface extending on the back plate between the ports. Having the ports on the back plates allows very easy connections for the liquid through-put, and also simplifies sealing of the front window to the back plate.

A specific embodiment of the invention will now be described by way of example with reference to the accompanying drawings in which:

FIG. 2 is an exploded perspective view of the cell. The Figures are not to scale.

Figure 1:
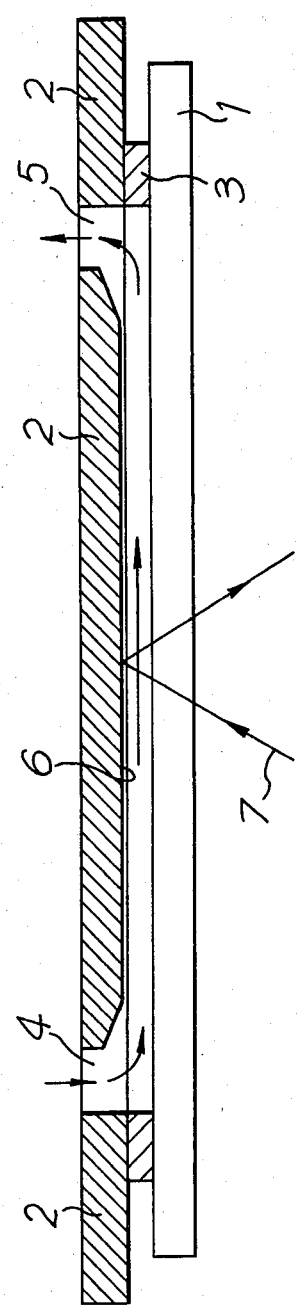
FIG. 1 is a sectional view through the cell.

In the drawings there is shown a first plate which is an optical window 1, a stainless steel back plate 2 and a sealing gasket 3 for positioning therebetween. The optical window 1 is clamped to the steel plate 2 with the gasket therebetween by conventional clamping means (not shown). The steel plate 2 has an inlet 4 for liquid and an outlet 5 for liquid and lying therebetween is a polished surface 6 suitable for reflecting an optical beam. The dimensions of the cell are suitably 15 mm in length, with a breadth of 6 mm and a thickness of 0.15 mm. The thickness can be varied by using different gaskets to vary the size of the gap between the optical window and the steel back plate. The gasket can suitably be made of P.T.F.E.

The reflecting surface of the back plate 2 can be slightly curved or tapered so that the path length across the cell changes. The change in path length is equal to or greater than the difference in wave lengths between the upper and lower limits of the range of radiation used. This leads to a condition of near uniform interference throughout the spectral range and results in the absence of interference fringe effects in the recorded spectrum.

Each of the inlet 4 and outlet 5 are formed as a circular hole on the outside of the back plate which tapers to an inclined triangular transition on the inside of the back plate, in the form of a right-angled equilateral triangle. This ensures smooth flow throughout the cell.

Particular advantages of this cell are that with a very simple construction it has a very small volume, of the order of microliters, and that an optical beam shown schematically at 7 is reflected back from the mirrored wall of the cell and passes through volume of liquid twice. This arrangement gives extra sensitivity and allows detection of very small quantities of material present in the flow. It can be used for example, as an auxiliary specific detector for liquid chromatography. The dimensions of the cell embodiment given above are suitable for it being used with known commercial spectrometers. The optical systems used will of course require adapting so that the spectrometer beam is passed into the cell and the reflected beam from the cell is passed onto the spectrometer for analysis.

The cell is particularly suitable for detecting transient constituents in flowing liquids. With the chosen dimensions minimum mixing occurs during passage of the liquid through the cell. This is assisted by shaping of the inlet and outlet.

The optical transmission of the complete device is about 60% in the infra-red range. If desired the reflecting surface can have a special coating to increase reflectivity.

I claim:

1. A liquid cell for use in spectroscopic analysis of flowing liquids formed by a front plate as an optical window, a back plate having spaced apart apertures therein, a tapered reflecting surface on the back plate between the apertures, and a sealing means between said two plates, each of said apertures being an entry and an exit port, respectively, for liquids to the cell.

2. A liquid cell according to claim 1 wherein said entry and exit ports are formed as a circular hole on the outside of said back plate which opens to a triangular taper on the inside of said back plate.

3. A liquid cell according to claim 1 wherein the dimensions of said cell are about 15 mm in length, a breath of about 6 mm and a thickness of about 0.15 mm.

4. A liquid cell according to claim 1 wherein the back plate is metal.

5. A liquid cell according to claim 1 wherein said reflecting surface has a coating to increase reflectivity.

6. A liquid cell according to claim 1 wherein the reflecting surface is non-parallel with the window whereby the path length between them varies along the cell.

7. A liquid cell according to claim 6 wherein the degree of variation of path length corresponds to the difference in wave length of the upper and lower wave lengths of the radiation used.

8. A liquid cell according to claim 1 wherein said sealing means being polytetrafluoroethylene.

9. A liquid cell for use in spectroscopic analysis of flowing liquids formed by a front plate as an optical window, a back plate having an inlet port and an outlet port, a tapered reflecting surface between said ports, and a sealing means between said two plates, said plates being removably attached to said sealing means by clamping means.

10. A liquid cell according to claim 9 wherein said cell being adapted to contain a volume of liquid in the microliter range.

* * * * *